US009943826B2

(12) United States Patent
Haynes et al.

(10) Patent No.: US 9,943,826 B2
(45) Date of Patent: Apr. 17, 2018

(54) POROUS SILICA HAVING HIGH PORE VOLUME AND METHODS OF MAKING AND USING SAME (71) Applicant: REGENTS OF THE UNIVERSITY OF MINNESOTA, Minneapolis, MN (US)

(72) Inventors: Christy Lynn Haynes, Minneapolis, MN (US); Samuel Michael Egger, Roseville, MN (US); Ashish Datt, Ithaca, NY (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 401 days.

(21) Appl. No.: 14/497,796

(22) Filed: Sep. 26, 2014

(65) Prior Publication Data
US 2016/0193588 A1 Jul. 7, 2016

Related U.S. Application Data (60) Provisional application No. 61/882,879, filed on Sep. 26, 2013.

(51) Int. Cl.
*B01J 20/28* (2006.01)
*B01J 21/08* (2006.01)
*B01J 35/02* (2006.01)
*B01J 37/00* (2006.01)
*B01J 20/10* (2006.01)
*B01J 20/30* (2006.01)
*G01N 21/65* (2006.01)
*B01D 53/02* (2006.01)

(52) U.S. Cl.
CPC ........ *B01J 20/28021* (2013.01); *B01D 53/02* (2013.01); *B01J 20/103* (2013.01); *B01J 20/3057* (2013.01); *B01J 21/08* (2013.01); *B01J 35/026* (2013.01); *B01J 37/0018* (2013.01); *B01J 37/0072* (2013.01); *G01N 21/658* (2013.01); *B01D 2253/106* (2013.01)

(58) Field of Classification Search
CPC .... B01J 20/28021; B01J 21/08; B01J 35/026; B01J 37/0018; B01J 37/0072; B01J 20/103; B01J 20/3057; G01N 21/658; B01D 53/02; B01D 2253/106
See application file for complete search history.

(56) References Cited

U.S. PATENT DOCUMENTS

| 7,132,165 | B2 * | 11/2006 | Pinnavaia | C01B 37/02 423/326 |
| 8,048,394 | B2 | 11/2011 | Yano et al. | |
| 8,440,229 | B2 | 5/2013 | Trogler et al. | |
| 8,449,856 | B2 | 5/2013 | Yano et al. | |
| 9,567,265 | B2 * | 2/2017 | Slowing | C07C 1/22 |
| 2009/0311332 | A1 | 12/2009 | DeShong et al. | |
| 2010/0069237 | A1 * | 3/2010 | Yano | B01J 20/103 502/439 |

FOREIGN PATENT DOCUMENTS

| WO | 2007/017843 A2 | 2/2007 |
| WO | 2009/078924 A2 | 6/2009 |
| WO | 2012/051341 A1 | 4/2012 |

OTHER PUBLICATIONS

Nandy et al., J. Sol-Gel Science and Technology, 72(1), pp. 49-55 (2014).*
Egger, "Ultraporous Mesostructured Silica Nanoparticles" Apr. 2015 *Chem. Mater.*, 27:3193-3196; Supporting Information, 1-17.
Atkinson et al., "Advanced anodes for high-temperature fuel cells," *Nature Materials*, Jan. 2004; 3:17-27.
Bergmann et al., "Solving the generalized indirect Fourier transformation (GIFT) by Boltzmann simplex simulated annealing (BSSA)," *Journal of Applied Crystallography*, Oct. 2000; 33:1212-1216.
Blin et al., "Pore size engineering of mesoporous silicas using decane as expander," *Langmuir*, May 2, 2000; 16(9):4229-4236.
Branton et al., "Physisorption of argon, nitrogen and oxygen by MCM-41, a model mesoporous adsorbent," *Journal of the Chemical Society, Faraday Transactions*, Oct. 7, 1994; 90(19):2965-2967.
"Cetrimonium bromide," *Wikipedia*, last modified Sep. 19, 2013. Retrieved from the Internet on Sep. 23, 2013; http://en.wikipedia.org/wiki/Cetyl trimethylammonium bromide; 3 pages.
Chen et al., "Construction of Homogenous/Heterogeneous Hollow Mesoporous Silica Nanostructures by Silica-Etching Chemistry: Principles, Synthesis, and Applications," *Accounts of Chemical Research*, 2014; 47(1):125-137.
Chong et al., "Functionalization of SBA-15 with APTES and Characterization of Functionalized Materials," *The Journal of Physical Chemistry B*, Sep. 20, 2003; 107(46):12650-12657.
Colombo, "Materials science. In praise of pores," *Science*, Oct. 17, 2008; 322(5900):381-383.
Davis, "Ordered porous materials for emerging applications," *Nature*, Jun. 20, 2002; 417:813-821.
De Miguel et al., "Structure, Morphology, Physical Formats and Characterization of Polymer Supports," Chapter 1 in *Polymeric Materials in Organic Synthesis and Catalysis*, Wiley-VCH Verlag GmbH & Co. KGaA, Weinheim, FRG, Jul. 10, 2003:1-52. Available online Jan. 28, 2005.
Farha et al., "Metal-Organic Framework Materials with Ultrahigh Surface Areas: Is the Sky the Limit?," *Journal of the American Chemical Society*, 2012; 134(36):15016-15021. Available online Aug. 20, 2012.

(Continued)

Primary Examiner — Robert S Cabral
(74) Attorney, Agent, or Firm — Mueting, Raasch & Gebhardt, PA (57) ABSTRACT

Silica particles, and methods of making and using silica particles are disclosed herein. In some embodiments, the silica particles are hollow, include an outer shell portion having a mesoporous structure, and have a pore volume of at least 4 cm$^3$/g. In some embodiments, the silica particles include an outer shell portion having a mesoporous structure forming a cavity, the silica particles have an average pore diameter of 3 to 100 nm, and at least a portion of the silica particles include one or more core nanoparticles within the cavity. Silica particles as disclosed herein can be useful in a wide variety of applications such as selective separations (e.g., gas separations or purifications) based on structure.

21 Claims, 6 Drawing Sheets

(56) References Cited

OTHER PUBLICATIONS

Fuertes et al., "Synthesis of colloidal silica nanoparticles of a tunable mesopore size and their application to the adsorption of biomolecules," *J Colloid Interf Sci*, Sep. 1, 2010; 349(1):173-180.
Furukawa et al., "The Chemistry and Applications of Metal-Organic Frameworks," *Science*, Aug. 30, 2013; 341:6149.
Glatter, "A new method for the evaluation of small-angle scattering data," *Journal of Applied Crystallography*, Oct. 1, 1977; 10:415-421.
Glatter, "The interpretation of real-space information from small-angle scattering experiments," *Journal of Applied Crystallography*, Apr. 1, 1979; 12:166-175.
Jiao et al., "Synthesis of discrete and dispersible hollow mesoporous silica nanoparticles with tailored shell thickness for controlled drug release," *Journal of Materials Chemistry*, Sep. 14, 2012; 22(34):17636-17643.
Jun et al., "Synthesis of New, Nanoporous Carbon with Hexagonally Ordered Mesostructure," *Journal of the American Chemical Society*, 2000; 122(43):10712-10713. Available online Oct. 12, 2000.
Kunieda et al., "Effect of Oil on the Surfactant Molecular Curvatures in Liquid Crystals," *J Phys Chem B*, Jan. 29, 1998; 102(5):831-838.
Lin et al., "Impacts of Mesoporous Silica Nanoparticle Size, Pore Ordering, and Pore Integrity on Hemolytic Activity," *Journal of the American Chemical Society*, 2010; 132(13):4834-4842. Available online Mar. 15, 2010.
Lin et al., "Stability of small mesoporous silica nanoparticles in biological media," *Chem Commun*, Jan. 2011; 47:532-534. Available online Nov. 16, 2010.
Lin et al., "Critical Considerations in the Biomedical Use of Mesoporous Silica Nanoparticles," *The Journal of Physical Chemistry Letters*, Jan. 11, 2012; 3(3):364-374.
"Mesoporous material," *Wikipedia*, last modified on Apr. 5, 2013. Retrieved from the Internet on Sep. 23, 2013; http://en.wikipedia.org/wiki/Mesoporous_material; 2 pages.
Meylan et al., "Atom/fragment contribution method for estimating octanol-water partition coefficients," *J. Pharm. Sci.*, Jan. 1995; 84(1):83-92. Available online Sep. 17, 2006.
Minakuchi, et al., "Octadecylsilylated Porous Silica Rods as Separation Media for Reversed-Phase Liquid Chromatography," *Analytical Chemistry*, Oct. 1, 1996; 68(19):3498-3501.
"N,N-Dimethylhexadecylamine," copyright 2013, Sigma-Aldrich Co, LLC. Retrieved from the Internet on Sep. 23, 2013; http://www.sigmaaldrich.com/catalog/product/aldrich/40460?lang=en&region=US ; 2 pages.
Smarsly et al., "SAXS analysis of mesoporous model materials: a validation of data evaluation techniques to characterize pore size, shape, surface area, and curvature of the interface," *Scattering Methods and the Properties of Polymer Materials*, Springer Berlin Heidelberg, 2005; 130:105-113. Available online Jun. 3, 2005.
Tanev et al., "Titanium-containing mesoporous molecular sieves for catalytic oxidation of aromatic compounds," *Nature*, Mar. 24, 1994; 368(6469):321-323.
Ulagappan et al., "Evidence for supramolecular organization of alkane and surfactant molecules in the process of forming mesoporous silica," *Chem Commun*, 1996; 24:2759-2760.
Vallet-Regi et al., "Mesoporous materials for drug delivery," *Angew Chem Int Ed Engl*, Oct. 4, 2007; 46(40):7548-7558.
Wang et al., "Silica Hollow Spheres with Ordered and Radially Oriented Amino-Functionalized Mesochannels," *Chem Mater*, 2009; 21(4):612-620. Available online Jan. 20, 2009.
Wu et al., "Synthesis of mesoporous silica nanoparticles," *Chem Soc Rev*, May 7, 2013; 42(9):3862-3875. Available online Feb. 12, 2013.
Wu et al., "Compartmentalized Hollow Silica Nanospheres Templated from Nanoemulsions," *Chem Mater*, 2013; 25(3):352-364. Available online Jan. 9, 2013.
Yang et al., "$SiO_2$@$YBO_3$:$Eu^{3+}$ Hollow Mesoporous Spheres for Drug Delivery Vehicle," *ACS Appl. Mater. Interfaces*, 2013; 5(12):5788-5796. Available online May 24, 2013.
Zhang et al., "Multiple Morphologies and Characteristics of "Crew-Cut" Micelle-like Aggregates of Polystyrene-b-poly(acrylic acid) Diblock Copolymers in Aqueous Solutions," *Journal of the American Chemical Society*, 1996; 118(13):3168-3181. Available online Apr. 3, 1996.
Zhang et al., "Facile Large-Scale Synthesis of Monodisperse Mesoporous Silica Nanospheres with Tunable Pore Structure," *Journal of the American Chemical Society*, 2013; 135(7):2427-2430.
Zhu et al., "Stimuli-Responsive Controlled Drug Release from a Hollow Mesoporous Silica Sphere/Polyelectrolyte Multilayer Core-Shell Structure," *Angewandte Chemie*, Aug. 12, 2005; 44(32):5083-5087. Available online Jul. 14, 2005.

\* cited by examiner

POROUS SILICA HAVING HIGH PORE VOLUME AND METHODS OF MAKING AND USING SAME

This application claims the benefit of U.S. Provisional Application No. 61/882,879, filed Sep. 26, 2013, which is herein incorporated by reference in its entirety.

GOVERNMENT FUNDING

This invention was made with government support under HR0011-13-2-0002 awarded by Defense Advanced Research Projects Agency. The government has certain rights in the invention.

BACKGROUND

Mesoporous silica nanomaterials find use in a variety of applications such as catalysis, separations, drug delivery, and gas adsorption wherein a large pore volume is advantageous. The pores in these materials are formed based on a surfactant template assembled ahead of silica condensation. The highest pore volumes achieved to date have been synthesized by incorporating pore swelling agents such as decane or N,N-dimethylhexadecylamine (DMHA) with the standard cetyltrimethylammonium bromide (CTAB) surfactant.

Although metal organic frameworks (MOFs) demonstrate the highest reported pore volumes and surface areas to date, they suffer from thermal and hydrothermal instability. In contrast, ceramic materials are particularly well suited for harsh conditions such as high temperature or corrosive environments but have not attained the strikingly high pore volumes and surface areas of MOFs.

The need remains for materials with high pore volumes that are well suited for harsh conditions such as high temperature or corrosive environments.

SUMMARY

In one aspect, the present disclosure provides hollow silica particles including an outer shell portion having a mesoporous structure, wherein the silica particles have a pore volume of at least 4 $cm^3/g$ as determined by nitrogen physisorption at partial pressures of $P/P_o$ of 0.99. In certain embodiments, the silica particles have an average pore diameter of 3 to 100 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS). In certain embodiments, the silica particles have an average particle diameter of 20 to 10,000 nm as determined by dynamic light scattering (DLS), transmission electron microscopy (TEM), or scanning electron microscopy (SEM). In certain embodiments, the silica particles have a polydispersity index of 0.005 to 0.200 as determined by dynamic light scattering (DLS). In certain embodiments, the silica particles have an outer shell portion with an average thickness of 3 to 100 nm. In certain embodiments, the silica particles have a surface area of at least 1200 $m^2/g$ as measured by Brunauer-Emmett-Teller (BET) theory. In certain embodiments, the hollow silica particles exhibit a small angle x-ray scattering pattern in which one or more peaks are observed at a diffraction angle corresponding to a range of d=2 to 100 nm. In certain embodiments, the outer shell portion is produced from at least one silicon compound including at least one organic group. In certain embodiments, the ratio of the thickness of the outer shell portion of the hollow silica particles to the average particle diameter is 0.0003 to 0.8.

In another aspect, the present disclosure provides silica particles comprising an outer shell portion having a mesoporous structure forming a cavity, wherein the silica particles have an average pore diameter of 3 to 100 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS), and wherein at least a portion of the silica particles include one or more core nanoparticles within the cavity. The silica particles can contain a wide variety of core nanoparticles within the cavity. Exemplary core nanoparticles include gold nanoparticles, iron nanoparticles, silver nanoparticles, and/or semiconductor quantum dots. In certain embodiments, the silica particles can have an average particle diameter of 20 to 10,000 nm as determined by transmission electron microscopy (TEM), and a polydispersity index of 0.005 to 0.200 as determined by dynamic light scattering (DLS). In certain embodiments, the silica particles can have an outer shell portion with an average thickness of 3 to 100 nm. In certain embodiments, the silica particles can have a surface area of at least 1200 $m^2/g$ as measured by BET theory. In certain embodiments, the silica particles can exhibit a small angle x-ray scattering pattern in which one or more peaks are observed at a diffraction angle corresponding to a range of d=2 to 100 nm.

In another aspect, the present disclosure provides a method for producing silica particles including an outer shell portion having a mesoporous structure. The method includes: preparing an aqueous mixture of components including at least one quaternary ammonium salt, at least one hydrophobic organic compound, and an aqueous medium; sonicating the aqueous mixture; combining at least one silica source capable of forming a silanol compound by hydrolysis thereof with the sonicated aqueous mixture under conditions effective to form silica particles; and removing excess components. Optionally, the components for preparing the aqueous mixture can further include at least one tertiary amine. In some embodiments, at least a portion of the silica particles are hollow. In some embodiments the method further includes adding nanoparticles before or during sonication, and the method produces silica particles including an outer shell portion having a mesoporous structure forming a cavity, and wherein at least a portion of the silica particles include one or more core nanoparticles within the cavity.

Hollow silica particles can be useful in a wide variety of applications including, for example, catalysis (e.g., a support for a heterogeneous catalyst), an adsorbent (e.g., for gas separation, gas purification, or gas storage), drug delivery, environmental contaminant analysis, and high contrast biological/biomedical imaging.

Silica particles having one or more core nanoparticles within the cavity can be useful in a wide variety of applications including, for example, chemical sensing methods such as surface-enhanced Raman spectroscopy (SERS).

Definitions

As used herein, "porous silica" refers to silica having minute holes or interstices though which a liquid or gas may pass.

As used herein, "mesoporous structure" refers to a structure having pores with diameters of 2 to 50 nm.

As used herein, "hollow" silica particles refers to silica particles having a cavity within an outer shell. The cavity may be substantially empty or may contain other materials such as hydrophobic organic compounds.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present invention is not intended to describe each embodiment or every implementation of the present invention. Rather, a more complete understanding of the invention will become apparent and appreciated by reference to the following description and claims in view of the accompanying drawings. Further, it is to be understood that other embodiments may be utilized and structural changes may be made without departing from the scope of the present invention.

DETAILED DESCRIPTION OF ILLUSTRATIVE EMBODIMENTS

For the last several decades, porous nanomaterials have garnered much scientific interest due to their extraordinary surface and textural properties, but the use of these porous materials has been practically limited by stability, scalability, and material homogeneity issues.

Herein, a new class of mesoporous silica nanomaterials that exhibit ultra-high pore volumes, large surface areas, and sub-100 nm primary particle size is disclosed. It is believed that this colloidal nanomaterial, which can exhibit pore volumes up to 4.5 cm$^3$/g or even greater, has the potential to be a robust platform for applications ranging from drug delivery to environmental remediation. The preparation of a new nanoscale mesoporous silica structural motif with unprecedented pore volumes to complement the small size, biocompatibility, and stability achieved with mesoporous silica is disclosed herein (e.g., Lin et al., *Chem Commun* 47, 532 (2011); and Lin et al., *The Journal of Physical Chemistry Letters* 3, 364 (2012)). This motif may be the result of a synergistic combination of swelling agents, stirring, and sonication, which completely changes the micellar arrangement during the synthesis and thus, the resulting colloidal nanoparticle. Various embodiments of these materials (e.g., the material designated as HLM-3) demonstrate pore volumes rivaling or surpassing those of the best metal organic frameworks (MOFs) currently published in the literature (NU-110) (e.g., Farha et al., *Journal of the American Chemical Society* 134, 15016 (2012)).

In one aspect, hollow silica particles including an outer shell portion having a mesoporous structure are disclosed herein. In some embodiments, the silica particles have a pore volume of at least 4 cm$^3$/g as determined by nitrogen physisorption at partial pressure (P/P$_o$) of 0.99. In certain embodiments, the silica particles have pore volume of at least 5 cm$^3$/g as determined by nitrogen physisorption at partial pressure (P/P$_o$) of 0.99. In other certain embodiments the silica particles have pore volume of at least 6 cm$^3$/g as determined by nitrogen physisorption at partial pressure (P/P$_o$) of 0.99.

In another aspect, silica particles comprising an outer shell portion having a mesoporous structure forming a cavity, wherein the silica particles have an average pore diameter of 3 to 100 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS), and wherein at least a portion of the silica particles include one or more core nanoparticles within the cavity, are disclosed herein. The silica particles can contain a wide variety of core nanoparticles within the cavity. Because the core nanoparticles can occupy the internal cavity, the overall pore volume will be typically be less than for the hollow silica particles that do not include core nanoparticles disclosed herein. Exemplary core nanoparticles include gold nanoparticles, iron nanoparticles, silver nanoparticles, and/or semiconductor quantum dots. Optionally, the core nanoparticles can be functionalized with a capture agent as desired (e.g., bis-boronic acids for glucose sensing) prior to being introduced into the reaction mixture for formation of the silica particles.

In some embodiments, the silica particles include a space between the silica shell and the core nanoparticle surface, forming pseudo "nano-rattle" structures that can be advantageous for sensing of large molecules.

In some embodiments, the silica particles have an average pore diameter of 3 to 100 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS). In certain embodiments, the silica particles have an average pore diameter of 10 to 80 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS). In other certain embodiments, the silica particles have an average pore diameter of 20 to 50 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS).

In some embodiments, the silica particles have an average particle diameter of 20 to 10,000 nm as determined by dynamic light scattering (DLS), transmission electron microscopy (TEM), or scanning electron microscopy (SEM). In certain embodiments, the silica particles have an average particle diameter of 30 to 5000 nm as determined by dynamic light scattering (DLS), transmission electron microscopy (TEM), or scanning electron microscopy (SEM). In other certain embodiments, the silica particles have an average particle diameter of 40 to 100 nm as determined by dynamic light scattering (DLS), transmission electron microscopy (TEM), or scanning electron microscopy (SEM). In various embodiments, the silica particles have a polydispersity index of 0.005 to 0.200 as determined by dynamic light scattering (DLS).

In some embodiments, the silica particles have an outer shell portion with an average thickness of 3 to 100 nm. In certain embodiments, the silica particles have an outer shell portion with an average thickness of 10 to 80 nm. In other certain embodiments, the silica particles have an outer shell portion with an average thickness of 20 to 50 nm.

In some embodiments, the silica particles have a surface area of at least 1200 $m^2/g$ as measured by BET theory. In certain embodiments, the silica particles have a surface area of at least 2000 $m^2/g$ as measured by BET theory. In other certain embodiments, the silica particles have a surface area of at least 3000 $m^2/g$ as measured by BET theory.

In certain embodiments, the silica particles exhibit a small angle x-ray scattering pattern in which one or more peaks are observed at a diffraction angle corresponding to a range of d=2 to 100 nm.

In some embodiments, the outer shell portion is produced from at least one silicon compound including at least one organic group. In certain embodiments, the ratio of the thickness of the outer shell portion of the silica particles to the average particle diameter is 0.0003 to 0.8. In other certain embodiments, the ratio of the thickness of the outer shell portion of the silica particles to the average particle diameter is 0.01 to 0.6. In still other certain embodiments, the ratio of the thickness of the outer shell portion of the silica particles to the average particle diameter is 0.1 to 0.5.

A facile, scalable method for the synthesis of a mesoporous silica nanoparticle platform which shows the robust performance of ceramics while presenting ultra-high pore volumes of 4.5 $cm^3/g$ or greater is disclosed herein. The ultra-high pore volumes are believed to be the highest of any known material.

Silica particles as disclosed herein can be made, for example, by the following method. In one embodiment, the method includes: preparing an aqueous mixture of components including at least one quaternary ammonium salt, at least one hydrophobic organic compound, and an aqueous medium (e.g., aqueous ammonium hydroxide); sonicating the aqueous mixture; combining at least one silica source capable of forming a silanol compound by hydrolysis thereof with the sonicated aqueous mixture under conditions effective to form silica particles; and removing excess components. Optionally, the components for preparing the aqueous mixture can further include at least one tertiary amine. In some embodiments, at least a portion of the silica particles are hollow.

In some embodiments the method further includes adding nanoparticles before or during sonication, and the method produces silica particles including an outer shell portion having a mesoporous structure forming a cavity, and wherein at least a portion of the silica particles include one or more core nanoparticles within the cavity. As used herein, a nanoparticle is a particle having at least one dimension (including, for example, diameter and pore size) of no more than 100 nm. A wide variety of core nanoparticles can be used including, for example gold nanoparticles, iron nanoparticles, silver nanoparticles, and/or semiconductor quantum dots. The nanoparticles can have a wide variety of shapes including, for example, nanospheres, nanorods, nanocubes, and the like. The presently disclosed methods utilize cationic vesicles (bilayers) of template that can favorably encapsulate negatively charged core particles, such as gold or iron. In certain embodiments, the presently disclosed method can quench aggregation of the core nanoparticles, and simultaneously provide them with long-term stability via silica coating. The presently disclosed emulsion method favorably aggregates the core nanoparticles into dimer and trimer morphologies, which are highly favorable for sensitive SERS detection of analytes. Such controlled aggregation of core nanoparticles can facilitate a spacer between the surface of the core nanoparticle-core nanoparticle contacts and the porous silica coating, which can be favorable for SERS sensing of large analytes such as proteins.

The at least one quaternary ammonium salt can be a compound represented by formula (1) and/or formula (2):

$$[R^1(CH_3)_3N]^+X^- \quad (1)$$

$$[R^1R^2(CH_3)_2N]^+X^- \quad (2),$$

wherein $R^1$ and $R^2$ are each independently a linear or branched alkyl group having 4 to 22 carbon atoms; and X is a monovalent anion.

In some embodiment, $R^1$ and $R^2$ each independently have 6 to 18 carbon atoms. In certain embodiment, $R^1$ and $R^2$ each have 8 to 16 carbon atoms. Examples of an alkyl group having 4 to 22 carbon atoms include various butyl groups, various pentyl groups, various hexyl groups, various heptyl groups, various octyl groups, various nonyl groups, various decyl groups, various dodecyl groups, various tetradecyl groups, various hexadecyl groups, various octadecyl groups and various eicosyl groups.

In some embodiments, X in the general formulae (1) and (2) is at least one monovalent anion selected from the group consisting of a halogen ion, a hydroxide ion, a nitrate ion, and a sulfate ion. In certain embodiments, X is a halogen ion. In other certain embodiments, X is a chlorine ion or a bromine ion. In still other certain embodiments, X is a bromine ion. In certain embodiments, X can be selected to increase crystallinity of the construction.

Examples of the alkyltrimethyl ammonium salts represented by the general formula (1) include, but are not limited to, butyltrimethyl ammonium chloride, hexyltrimethyl ammonium chloride, octyltrimethyl ammonium chloride, decyltrimethyl ammonium chloride, dodecyltrimethyl ammonium chloride, tetradecyltrimethyl ammonium chloride, hexadecyltrimethyl ammonium chloride, stearyltrimethyl ammonium chloride, butyltrimethyl ammonium bromide, hexyltrimethyl ammonium bromide, octyltrimethyl ammonium bromide, decyltrimethyl ammonium bromide, dodecyltrimethyl ammonium bromide, tetradecyltrimethyl ammonium bromide, hexadecyltrimethyl ammonium bromide, stearyltrimethyl ammonium bromide, and combinations thereof. For some embodiments, preferred alkyltrimethyl ammonium salts include alkyltrimethyl ammonium bromides and alkyltrimethyl ammonium chlorides. For some certain embodiments, preferred alkyltrimethyl ammonium salts include dodecyltrimethyl ammonium bromide and dodecyltrimethyl ammonium chloride.

Examples of the dialkyldimethyl ammonium salts represented by the general formula (2) include, but are not limited to, dibutyldimethyl ammonium chloride, dihexyldimethyl ammonium chloride, dioctyldimethyl ammonium chloride, dihexyldimethyl ammonium bromide, dioctyldimethyl ammonium bromide, didodecyldimethyl ammonium bromide, ditetradecyldimethyl ammonium bromide, and combinations thereof.

In some embodiments, preferred quaternary ammonium salts include, but are not limited to, cetrimonium bromide (i.e., cetyltrimethylammonium bromide, CTAB), alkyldimethylbenzylammonium chloride (ADBAC), benzethonium chloride, dimethyldioctadecylammonium chloride, tetramethylammonium hydroxide (TMAH or TMAOH), sodium dodecylsulfate, Gemini ammonium surfactants, and combinations thereof.

The optional at least one tertiary amine can be a compound represented by formula (3) and/or formula (4):

$$R^1(CH_3)_2N \quad (3)$$

$$R^1R^2(CH_3)N \quad (4),$$

wherein $R^1$ and $R^2$ are each independently a linear or branched alkyl group having 4 to 22 carbon atoms. In some embodiment, $R^1$ and $R^2$ each independently have 6 to 18 carbon atoms. In certain embodiment, $R^1$ and $R^2$ each have 8 to 16 carbon atoms. Examples of an alkyl group having 4 to 22 carbon atoms include various butyl groups, various pentyl groups, various hexyl groups, various heptyl groups, various octyl groups, various nonyl groups, various decyl groups, various dodecyl groups, various tetradecyl groups, various hexadecyl groups, various octadecyl groups and various eicosyl groups.

Exemplary tertiary amines include, but are not limited to, N,N-dimethylhexadecylamine (DMHA), N,N-dimethyloctadecylamine (DMOA), N,N-dimethyltetradecylamine, and combinations thereof.

A wide variety of hydrophobic organic compounds can be used in the methods disclosed herein. As used herein, a hydrophobic organic compound refers to a compound having a low solubility in water and capable of forming a separate phase from water. A hydrophobic organic compound is preferably a compound capable of being dispersed in the presence of quaternary ammonium salts as disclosed herein. Examples of the hydrophobic organic compound include compounds having a Log $P_{ow}$ value of 1 or more and preferably from 2 to 25. The "Log value" as used herein means a 1-octanol/water partition coefficient of a chemical substance, and is expressed by a numerical value calculated according to log $K_{ow}$ method. More specifically, a chemical structure of a compound is separated into constitutional fragments, and hydrophobic fragment constants of the respective fragments are accumulated to obtain the Log P value. See, for example, Meylan et al., *J. Pharm. Sci.*, 84:83-92 (1995).

Examples of hydrophobic organic compound include, but are not limited to, hydrocarbon compounds, ester compounds, fatty acids having 6 to 22 carbon atoms, alcohols having 6 to 22 carbon atoms, oil agents such as silicone oils, functional materials such as perfume components, base materials for agricultural chemicals, medical base materials, and combinations thereof.

Examples of hydrocarbon compounds include, but are not limited to, liquid paraffin or liquid petroleum jelly, squarane, squalene, perhydrosqualene, trimethyl benzene, xylene, toluene, benzene, and combinations thereof. In some embodiments, squarane and/or squalene can be preferred hydrocarbon compounds.

Examples of the ester compounds include oils and fats such as glycerol esters of fatty acids having 6 to 22 carbon atoms. Specific examples of such oils and fats include, but are not limited to, mink oil, turtle oil, soybean oil, sweet almond oil, beauty leaf oil, palm oil, grape seed oil, sesame seed oil, corn oil, Parleam oil, Arara oil, rape seed oil, sunflower oil, cotton seed oil, apricot oil, castor oil, avocado oil, jojoba oil, olive oil, cereal embryo oil, and combinations thereof.

Further examples of ester compounds include condensates of a fatty acid having 4 to 22 carbon atoms and a monohydric alcohol or a polyhydric alcohol other than glycerol having 1 to 22 carbon atoms. Specific examples of such ester compounds include, but are not limited to, isopropyl myristate, isopropyl palmitate, butyl stearate, hexyl laurate, isononyl isononanoate, 2-ethylhexy palmitate, 2-hexyldecyl laurate, 2-octyldecyl palmitate, 2-octyldodecyl myristate, and combinations thereof.

Further examples of ester compounds include esters of a polycarboxylic acid compound and an alcohol. Specific examples of such ester compounds include, but are not limited to, diisopropyl adipate, 2-octyldodecyl lactate, 2-diethylhexyl succinate, diisostearyl malate, glyceryl triisostearate, diglyceryl triisostearate, and combinations thereof.

Examples of fatty acid having 6 to 22 carbon atoms include, but are not limited to, myristic acid, palmitic acid, stearic acid, behenic acid, oleic acid, linoleic acid, linolenic acid, isostearic acid, and combinations thereof.

Examples of alcohols having 6 to 22 carbon atoms include, but are not limited to, cetanol, stearyl alcohol, oleyl alcohol, linoleyl alcohol, linolenyl alcohol, isostearyl alcohol, octyl dodecanol, and combinations thereof. Polyhydric alcohols derived from these alcohols may also be used in the present invention.

Examples of silicone oils include, but are not limited to, polydimethylsiloxane (PDMS); polysiloxanes modified with fatty acids, fatty alcohols, or polyoxyalkylenes; fluorosilicones; perfluorosilicone oils; and combinations thereof.

Polydimethylsiloxanes (PDMS) can be a phenylated product such as phenyl trimethicone, or may optionally be substituted with an aliphatic group and/or an aromatic group. These compounds may be in the form of a hydrocarbon-based oil or a silicone oil, and are preferably in the form of a linear or cyclic silicone having 2 to 7 silicon atoms and optionally containing an alkyl group or an alkoxy group which may be present in a pendant form in a silicone chain or at a terminal end thereof. In some embodiments, preferred siloxanes can include octamethyl cyclotetrasiloxane, decamethyl cyclopentasiloxane, hexadecamethyl cyclohexasiloxane, heptamethylhexyl trisiloxane, heptamethyloctyl trisiloxane, and combinations thereof.

Examples of perfume components as functional materials include natural perfumes and synthetic perfumes. Specific examples of the natural perfumes include, but are not limited to, spearmint oil, peppermint oil, citronella oil, *eucalyptus* oil, cascarilla oil, birch oil, cinnamon oil, clove oil, garlic oil, peppermint oil, majoram oil, nutmeg oil, palmarosa oil, *perilla* oil, rose oil, savory oil, rosemary oil, lavender oil, and combinations thereof. Specific examples of the synthetic perfumes include, but are not limited to, amyl acetate, amylcinnamic aldehyde, isoamyl salicylate, anisaldehyde, benzyl acetate, benzyl alcohol, borneol, 1-carvone, menthol, citral, citronellal, citronellol, coumarin, eugenol, methyl salicylate, vanillin, terpineol, and combinations thereof.

Hydrophobic organic compounds can be used singly or in the form of a mixture of any two or more thereof at any optional proportions. In addition, there may also be used such a hydrophobic organic compound in which a compound incapable of satisfying the above hydrophobic conditions is dissolved.

In certain preferred embodiments, the hydrophobic organic compound can be decane, squarane, squalene, perhydrosqualene, trimethyl benzene, triisopropyl benzene, isomers of xylene, toluene, benzene, a liquid paraffin, a liquid petroleum jelly, or a combination thereof.

Useful sonication conditions are further described herein. In brief, the sonication can be conducted, for example, at a temperature of 5 to 95° C., at frequencies of 5 to 100 kHz, for times of 5 to 1000 min, and with either table top or ultra-sonicator sonication equipment.

A silica source includes a compound (e.g., an alkoxysilane) that can produce a silanol through hydrolysis. The at least one silica source can be a compound represented by formulas (4), (5), (6), or (7):

$$R^3SiY_3 \qquad (4);$$

$$R^3{}_2SiY_2 \qquad (5);$$

$$R^3{}_3SiY \qquad (6); \text{ and}$$

$$Y_3Si\text{—}R^4\text{—}SiY_3 \qquad (7),$$

wherein $R^3$ groups are each independently an organic group having a carbon atom directly bonded to a silicon atom; $R^4$ is a hydrocarbon group having 1 to 4 carbon atoms or a phenylene group; and Y is a monovalent hydrolyzable group that can be hydrolyzed into a hydroxyl group.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the formation of the silica particles. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

In the general formulae (4) to (7), for some embodiments, the $R^3$ groups are each independently a hydrocarbon group having 1 to 22 carbon atoms in which a part of hydrogen atoms may optionally be substituted with a fluorine atom. Specific examples of $R^3$ include an alkyl group having 1 to 22 carbon atoms, an alkyl group having 4 to 18 carbon atoms, an alkyl group having 6 to 18 carbon atoms, an alkyl group having 8 to 16 carbon atoms, a phenyl group, a benzyl group, and combinations thereof. Specific examples of $R^4$ include an alkanediyl group having 1 to 4 carbon atoms (e.g., a methylene group, an ethylene group, a trimethylene group, a propane-1,2-diyl group, and a tetramethylene group) or a phenylene group. For some embodiments, Y is an alkoxy group having 1 to 22 carbon atoms. For certain embodiments, Y is an alkoxy group having 1 to 8 carbon atoms, For other certain embodiments, Y is an alkoxy group having 1 to 4 carbon atoms. For still other certain embodiments, Y is a halogen group other than fluorine.

Examples of the suitable silica sources include compounds trialkoxysilanes, dialkoxysilanes, and monoalkoxy silanes of the general formulae (4), (5), and (6) in which $R^3$ is a phenyl group, a benzyl group, or a hydrocarbon group having 1 to 20 carbon atoms. In some embodiments, $R^3$ is a hydrocarbon group having 1 to 10 carbon atoms. In certain embodiments, $R^3$ is a hydrocarbon group having 1 to 5 carbon atoms. In some certain embodiments, some of the hydrogen atoms may optionally be substituted with fluorine atoms. Compounds of the general formula (7) include, but are not limited to, compounds in which Y is a methoxy group, and $R^4$ is a methylene group, an ethylene group, or a phenylene group.

For certain embodiments, preferred silica sources can include tetramethoxysilane, tetraethoxysilane, phenyl triethoxysilane, 1,1,1-trifluoropropyl triethoxysilane, and combinations thereof.

Conditions effective to form silica particles can include a temperature of 5 to 95° C. with agitation (e.g., stirring). Other conditions that may be effective to form the silica particles are disclosed in PCT International Publication No. WO 2012/051341 A1 (Haynes et al.) and U.S. Pat. No. 8,048,394 B2 (Yano et al.) and U.S. Pat. No. 8,449,856 B2 (Yano et al.).

Excess components can then be removed by a wide variety of methods including, but not limited to, solvent extraction methods and heating methods (e.g., heating the silica particles at a temperature of 50 to 1200° C.).

The hollow silica particles can be useful in a wide variety of applications including, for example, catalysis (e.g., a support for a heterogeneous catalyst), an adsorbent (e.g., for gas separation, gas purification, or gas storage), drug delivery, and environmental contaminant analysis.

Figure 1:
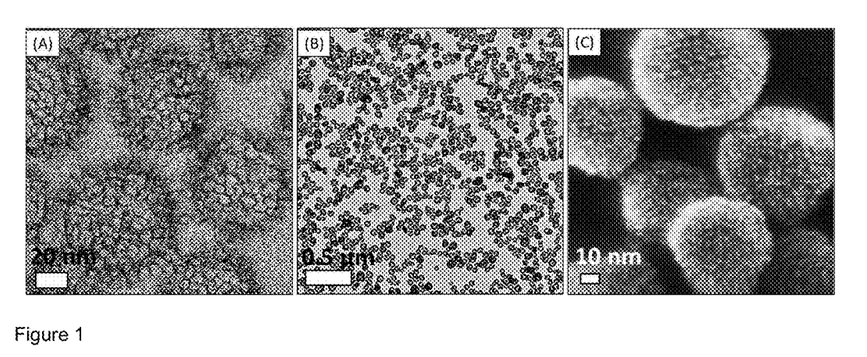
FIG. 1 illustrates electron microscopy images of the exemplary material designated as HLM-3. (A-B) Transmission Electron Microscopy (TEM) shows textural porosity and high monodispersity. (C) Scanning electron microscopy (SEM) displays surface structure.
Figure 2:
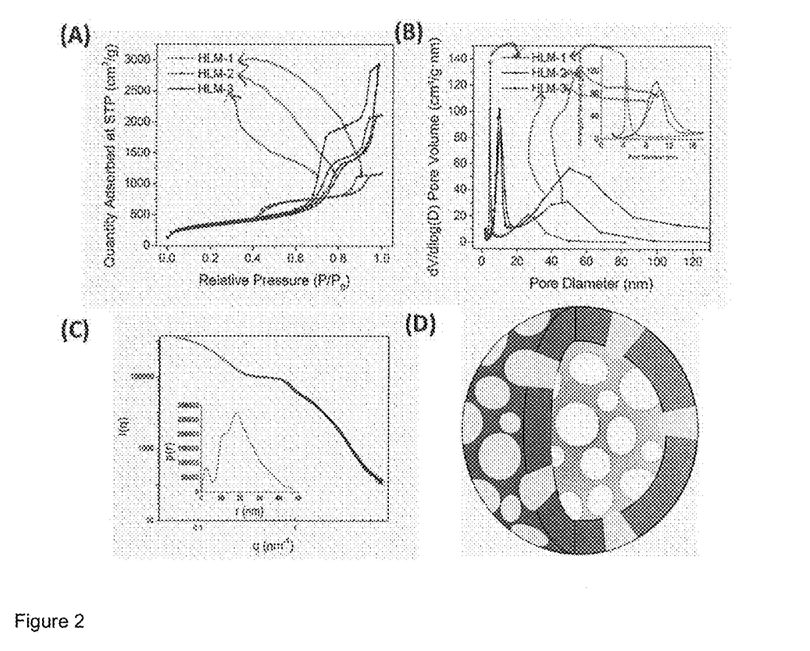
FIG. 2 illustrates nitrogen adsorption-desorption and small angle x-ray scattering measurements demonstrating the tiered porosity of exemplary materials. (A) Nitrogen isotherms for mesoporous silica nanostructures made by mixing a quaternary ammonium surfactant with decane-only, DMHA only, or both decane and DMHA (designated as HLM-3). (B) Barrett-Joyner-Halenda (BJH)-derivatized pore distribution plot for the three samples indicated in FIG. 2A (decane-only, DMHA only, and HLM-3). The inset shows details in the primary pore peak between 1 and 20 nm. (C) small angle x-ray scattering (SAXS) profile for HLM-3 and the corresponding paired distance distribution function (PDDF) as inset. (D) A diagram of the porous structure of HLM-3.

The extraordinary textural properties of the material designated as HLM-3 are shown in FIG. 1. Transmission electron microscopy (TEM) images display the hollow nature of this material by the distinct difference in contrast between the walls and the center of each particle. Image analysis reveals an average particle diameter of 71.3±13.4 nm. Nearly every particle analyzed displays an interior cavity, which was measured at 41.7±10.7, making for an average wall thickness of 15.0±3.6 nm. Each EM image was taken on particles that had been centrifuged at 66,000×g and resuspended. The paucity of broken or deformed structures shows these materials to be quite robust. This stability under extreme physical force may be due to the wall thickness, which is substantially larger than other reported hollow mesoporous silica structures (e.g., Zhu et al., *Angewandte Chemie* 117, 5213 (2005); and Chen et al., *Accounts of Chemical Research*, 47, 125-137 (2014)). The high monodispersity of these particles can be seen in a wide-field image (FIG. 1B). The lacey structure makes it difficult to size the wall pores by TEM, but the cavity measurements correlate well to $N_2$ physisorption-based pore size distributions and small angle x-ray scattering (SAXS) data (FIG. 2). The TEM size and monodispersity also agree well with DLS data (see SI). A high resolution SEM image shows the textural porosity present on the surface of these materials (FIG. 1C).

Nitrogen adsorption-desorption isotherms give further insight into the structural properties of these materials. Representative isotherms of nanoparticles generated using a CTAB template expanded with decane only (e.g., the material designated as HLM-1) or DMHA only (e.g., the material designated as HLM-2) are compared to the material designated as HLM-3 in FIG. 2A, demonstrating the combined effects of a co-surfactant (DMHA) and oil (decane) followed by sonication. When only decane is used, capillary condensation, indicative of mesopores, occurs at $P/P_0$=0.3. This condensation along with a type IV hysteresis curve (e.g., Branton et al., *Journal of the Chemical Society, Faraday Transactions* 90, 2965 (1994)) indicates pores of 4.38 nm diameter, typical of MCM-41 type materials synthesized with swelling agents. The plateau for the material designated as HLM-1 from $P/P_0$=0.95 to 1.0 indicates that interparticle void spaces have been completely filled with nitrogen, and also demonstrates the lack of any pores greater than 50 nm (macropores). These results for the material designated as HLM-1 are consistent with literature precedent. Both the DMHA-only sample (e.g., designated as HLM-2) and the material designated as HLM-3 show capillary condensation near $P/P_0$ of approximately 0.6. This increase is typical of SBA-type materials with pore diameters greater than 6 nm (e.g., Jun et al., *Journal of the American Chemical Society* 122, 10712 (2000)). Once multi-layer $N_2$ adsorption begins, the adsorption behavior of the two materials diverges. Although both samples display mixed H1-H3 type hysteresis curves (e.g., Miguel et al., T. Rohr, D. C. Sherrington, in *Polymeric Materials in Organic Synthesis and Catalysis*. (Wiley-VCH Verlag GmbH & Co. KGaA, 2005), pp. 1-52), the material designated as HLM-3 displays a "duck-shaped" hysteresis curve. This extra area indicates a greater number density of pores, which results in a large quantity of gas adsorption (2931 $cm^3/g$, compared to 1164 $cm^3/g$ for the material designated as HLM-1, and approximately 2000 $cm^3/g$ for NU-110, the highest-performing MOF to date) (e.g., Farha et al., *Journal of the American Chemical Society* 134, 15016 (2012)). In addition, the lack of plateauing from $P/P_0$=0.95 to 1.0 in the material designated as HLM-3 indicates a volume contribution from large mesopores, macropores, and interparticle void spaces. This new type of isotherm is present in various embodiments of the materials disclosed herein prepared using a variety of surfactant/oil ratios. All data presented are from one representative sample; see supplementary information for characterization of various other samples.

A BJH pore diameter plot derived from the $N_2$ physisorption data, shown in FIG. 2B, gives insight into the tiered porosity of the exemplary materials disclosed herein. All samples, including those with only decane (e.g., designated as HLM-1) or only DMHA (e.g., designated as HLM-2), display a peak between 3 and 11 nm, indicative of the cylindrical pores typically seen in mesoporous silica (e.g., Jun et al., *Journal of the American Chemical Society* 122, 10712 (2000)). An additional broad peak is visible at higher pore diameters for each sample. In typical mesoporous silica nanoparticles, this broad peak represents the interparticle voids (e.g., Zhang et al., *Journal of the American Chemical Society* 135, 2427 (2013)). However, in the case of the material designated as HLM-3, it can be argued that the peak represents both interparticle voids and intraparticle cavities (large meso- or macropores at the center of each particle). It can be seen that the large increase in pore volume for the material designated as HLM-3 is due to an increase in the large meso- or macroporous region from 20 to 60 nm. Dynamic light scattering (DLS) and transmission electron microscopy (TEM) measurements in Table 1 show that the particle diameters do not change substantially between sample conditions, so the increase in pore volume for the material designated as HLM-3 should not be attributed to larger interparticle voids caused by disordered packing. It is, rather, indicative of an increased number density of mesopores and the presence of a large cavity inside each mesoporous nanoparticle.

Figure 3:
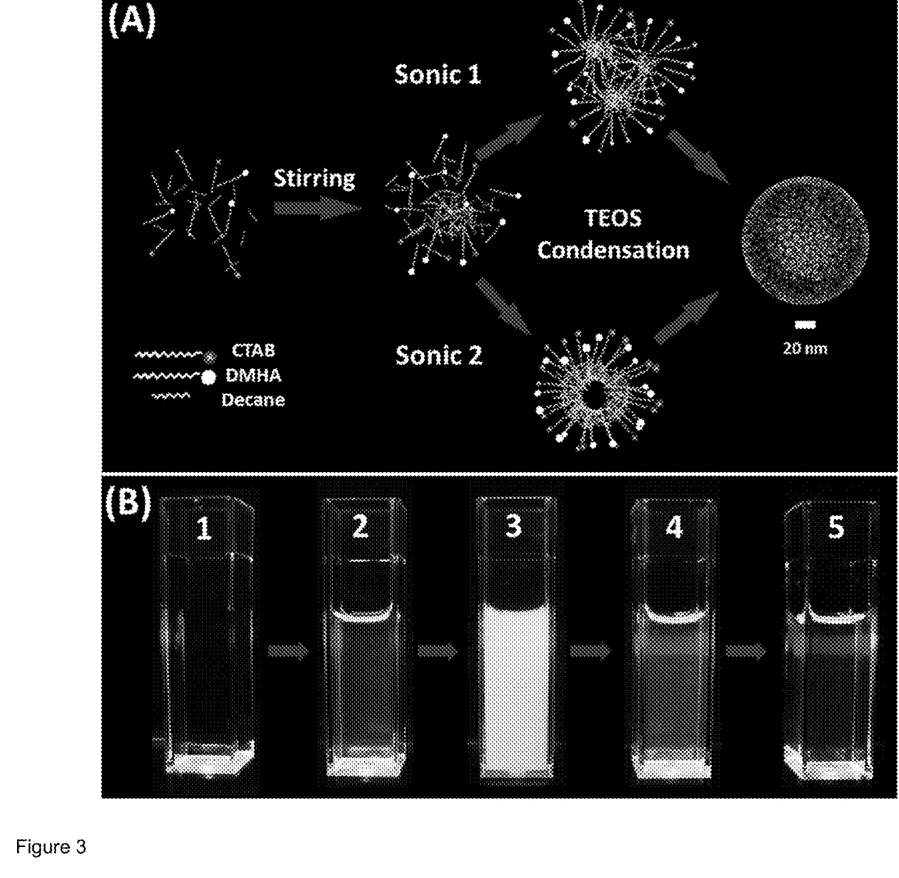
FIG. 3 illustrates (A) a schematic representation of the hypothesized micellar arrangement during the sonication for the surfactant/oil system; presented are two possibilities, Sonication Pathway 1 and Sonication Pathway 2, which illustrate oil and gas bubble cavity formation, respectively. (B) Representative images of various solutions during synthesis progress; cuvettes labeled 1, 2, 3, 4 and 5 contain water, synthesis media formulation, as-synthesized material, material after template removal (via dialysis), and purified product, respectively. Note: Cuvettes were irradiated with a 650 nm wavelength laser from right to left to highlight solution clarity.
Figure 4:
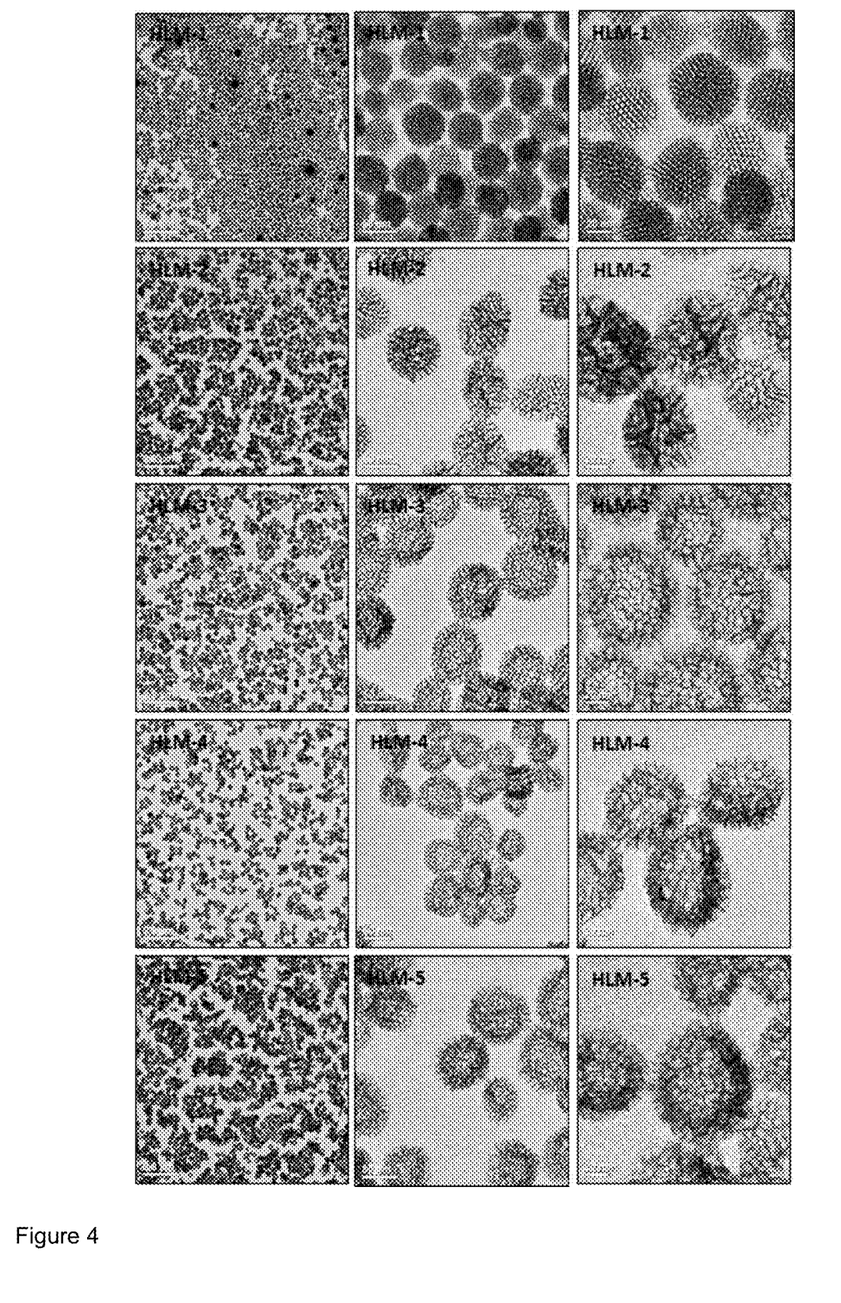
FIG. 4 illustrates TEM images of the exemplary materials designated as HLM 1-5. Left, middle, and right columns represent scale bars of 0.5 μm, 50 nm, and 20 nm, respectively. All TEM diameter measurements were taken by assessing 500 nanoparticles in each condition.
Figure 5:
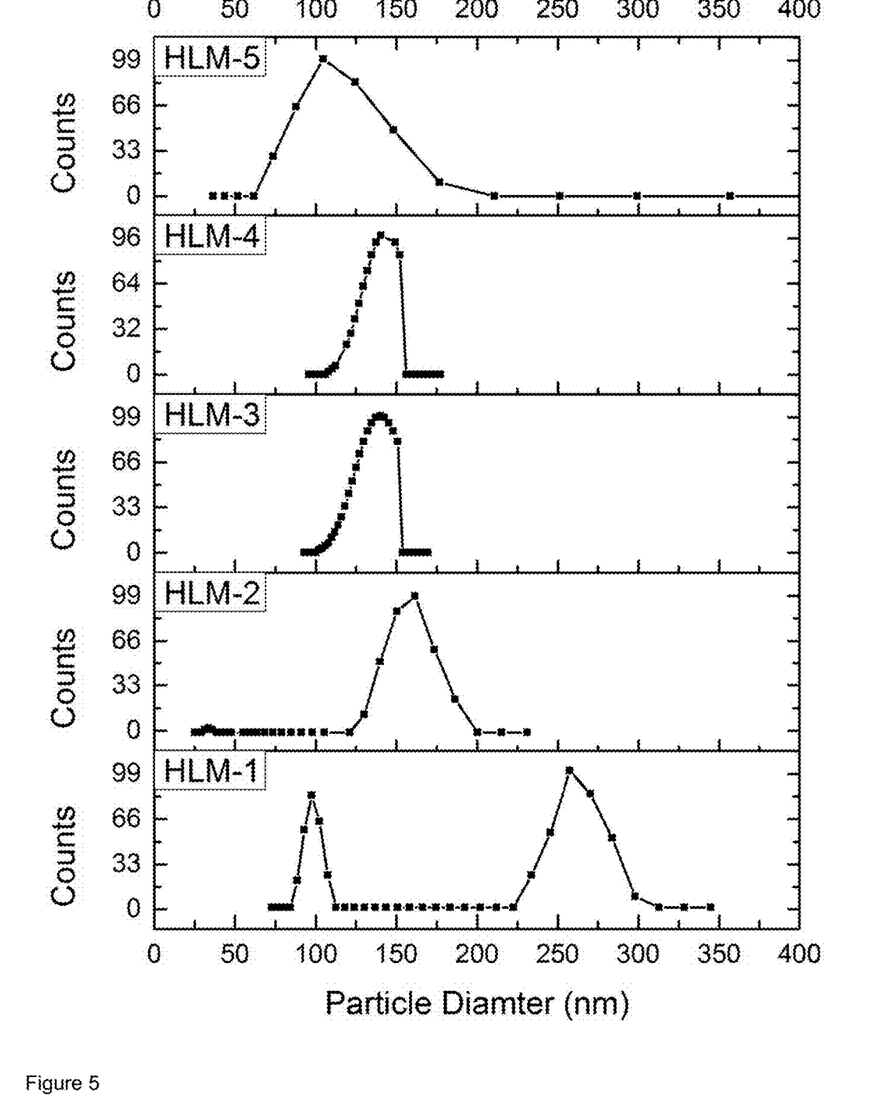
FIG. 5 illustrates dynamic light scattering data for exemplary materials showing the multimodal distribution.
Figure 6:
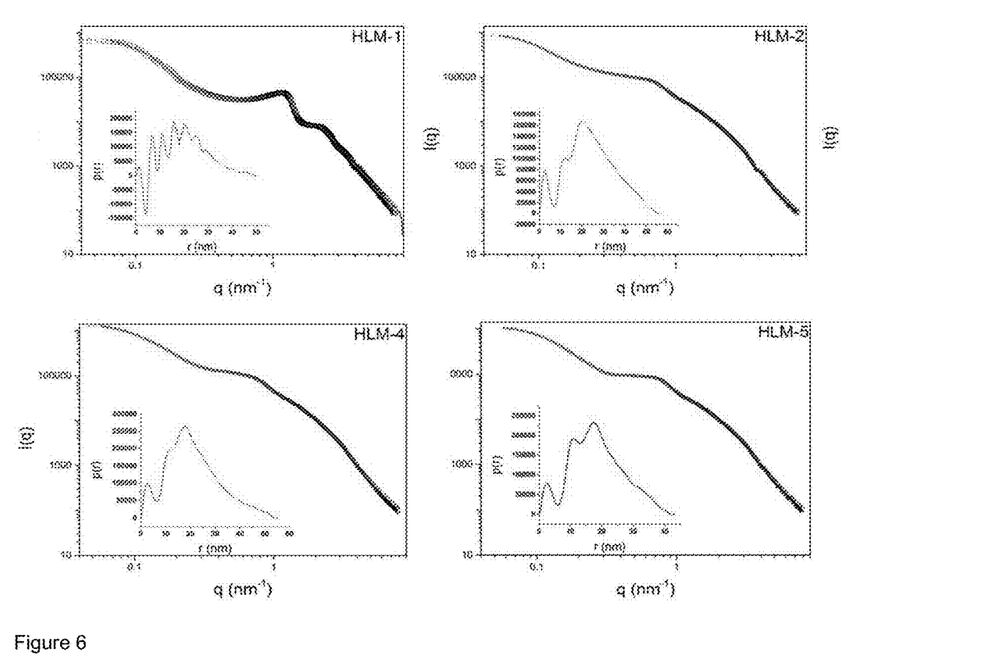
FIG. 6 illustrates SAXS profiles along with the pair distance distribution function (PDDF) plots for exemplary materials. The data for the material designated as HLM-3 is shown in the specification and is thus excluded here.
Figure 7:
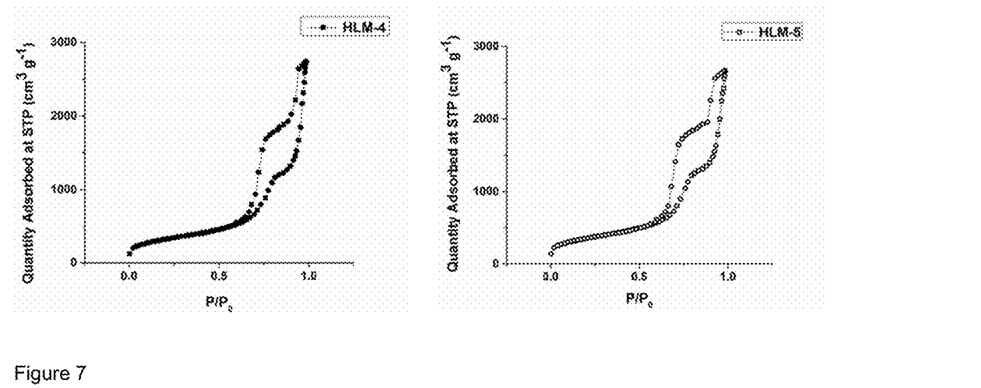
FIG. 7 illustrates nitrogen adsorption-desorption isotherms for the exemplary materials designated as HLM-4 and HLM-5. The isotherms for the materials designated as HLM-1, HLM-2, and HLM-3 are shown in the specification.

FIG. 2C shows the characteristic small angle x-ray scattering (SAXS) patterns for the material designated as HLM-3. There is a shoulder at q value of approximately 0.8 $nm^{-1}$, which is typical for large pore mesoporous silica materials, such as SBA-15 with a q value of approximately 1 $nm^{-1}$ (e.g., Chong et al., *The Journal of Physical Chemistry B* 107, 12650 (2003)). Desmearing of the profile reveals that this shoulder is indeed a peak (FIG. 6), as observed commonly in other mesoporous silicas (e.g., Chong et al., *The Journal* of *Physical Chemistry B* 107, 12650 (2003)). The higher order peaks at higher q values indicate the presence of short range order in the system. They do appear weaker than the primary peak, which can be attributed to the presence of lattice distortion in the mesoporous silica system. The inverse Fourier transform of the background-subtracted SAXS profile shows three different maxima, providing an additional insight into the different length scales present in the novel mesoporous silica material. The first maximum around 2.5 nm corresponds to the wall thickness between mesopores in agreement with previous work (e.g., Smarsly et al., in *Scattering Methods and the Properties of Polymer Materials*, (Springer Berlin Heidelberg, 2005), vol. 130, pp. 105-113). The second maximum, a shoulder around 12 nm, is attributed to the average pore size in the nanoparticle wall, a value which complements the nitrogen physisorption data (pore diameters of approximately 11 nm). Finally, the third maximum which comes around 20 nm is a convolution of a variety of length scale including the cavity size, the periodic nature of the pore network, polydispersity in the pore sizes, and lattice distortions in the material. Again, the broad feature at a length scale>20 nm agrees well with the nitrogen adsorption BJH pore size distribution data.

homogeneous and transparent. At least two hypotheses could explain this transformation. In both cases, the sonication can result in micellar perturbation, allowing new structures to form. In one hypothesis, the sonication generates bubbles which are stabilized by the oil and surfactant system. The gas becomes the basis for the hollow cavity once silica condenses at the oil-water interface. Alternatively (or in conjunction), a more significant micellar rearrangement could be taking place. DMHA can behave as a co-surfactant, so it is plausible that within each CTAB core, DMHA molecules are surrounding decane droplets to form a distribution of micellar aggregates (e.g., Wang et al., *Chem Mater* 21, 612 (2009); and Wu et al., *Chem Mater* 25, 352 (2013)). This concept is well-known in polymer chemistry when block co-polymers are used as structure-directing agents (e.g., Zhang et al., *Journal of the American Chemical Society* 118, 3168 (1996)). A pictorial representation of each hypothesized process is shown in FIG. 3.

In closing, the synthesis of a new class of porous silica materials which provide ultra-high pore volumes rivaling or surpassing the best performing porous materials is disclosed herein. This material is a versatile platform for diverse applications ranging from environmental remediation to

TABLE 1

Physicochemical properties of exemplary materials

| Sample | DMHA/ CTAB molar ratio | Decane/ CTAB molar ratio | Surface Area ($m^2/g$) | Pore Volume ($cm^3/g$) | TEM Particle Diameter (nm) | TEM Interior Cavity Diameter (nm) | Hydro- dynamic Diameter (nm) | Polydis- persity Index |
|---|---|---|---|---|---|---|---|---|
| HLM-1 | N/A | 1.5 | 1,161 | 1.8 | 65.2 (19.9) | — | 161.1 (0.7) | 0.192 (0.015) |
| HLM-2 | 1.3 | N/A | 1,131 | 3.3 | 85.4 (13.7) | — | 148.1 (2.1) | 0.100 (0.013) |
| HLM-3 | 1.3 | 1.5 | 1,235 | 4.5 | 71.3 (13.4) | 41.6 (10.7) | 136.2 (1.3) | 0.050 (0.031) |
| HLM-4 | 1.5 | 1.5 | 1,131 | 4.2 | 68.8 (13.3) | 42.1 (10.8) | 138.5 (1.1) | 0.058 (0.010) |
| HLM-5 | 1.3 | 2.0 | 1,221 | 4.1 | 77.9 (18.7) | 46.6 (15.2) | 108.1 (0.6) | 0.079 (0.038) |

The structure of these unusual materials is likely a result of micellar rearrangement prior to silica condensation. In the absence of swelling agents, mesoporous silica is typically synthesized through a surfactant-templated mechanism. Spherical CTAB micelles form in basic aqueous solution and serve as condensation sites for silica precursors. As condensation continues, the charge on the surface of the micelles is decreased, leading to a change in packing parameter and a transition to cylindrical micelles which form the basis for the pores (e.g., Wu et al., *Chem Soc Rev* 42, 3862 (2013)). When swelling agents such as DMHA or decane are added, they can disrupt the micellar structure, allowing for larger pores. DMHA can intercalate into the CTAB exterior and decane can localize among the hydrophobic CTAB tails (e.g., Kunieda et al., *J Phys Chem B* 102, 831 (1998); and Ulagappan et al., *Chem Commun*, (24) 2759 (1996)). In the case of the material designated as HLM-3, a sonication step can provide a micellar rearrangement that can result in the final hollow template. This rearrangement is visually apparent in the opacity of the reaction suspension over time (FIG. 3B). With stirring only, the micellar suspension is cloudy and opaque, suggesting that the micelles are neither uniform nor well-dispersed. When the solution is sonicated for 90 minutes and allowed to sit overnight, it becomes much more biomedical sensing. The facile and cost effective nature of the synthetic process can allow for reasonable scale up and use in emerging applications. The hierarchical porosity of this material may lend itself to further study and new applications.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials

All reagents were used as received and without further purification. Hexadecyltrimethylammonium bromide (CTAB, 99%), N,N-dimethylhexadecyl amine (DMHA, >95%), and tetraethylortho silicate (TEOS, 98%) were purchased from Sigma Aldrich. Decane (>99%) was purchased from TCI America. Aqueous ammonium hydroxide ($NH_4OH$, 28-30%) was purchased from Macron Fine Chemicals. Both 95 and 99% ethanol were purchased from Decon Labs, Inc. The water used in these experiments was purified by a Millipore Milli-Q system equipped with a 0.22 μm Milli-pak filter.

Characterization

Nitrogen adsorption-desorption isotherms were collected with a Micromeritics ASAP 2020 system at 77K. Powdered samples of 50-100 mg were degassed at 120° C. for 6 hours prior to measurement. Barrett-Joyner-Halenda (BJH)/Kruk-Jaroniec-Sayari (KJS) models were used to calculate pore volume and surface area. Total pore volume calculations were taken from the total quantity of nitrogen adsorbed at a partial pressure ($P/P_o$) of 0.99. Dynamic light scattering measurements were performed with a Brookhaven Instruments Zeta PALS system at 25° C. Samples were measured as direct aliquots from reaction suspensions or at 1 mg/mL for purified nanoparticles. Transmission electron microscopy (TEM) images were collected on a FEI Tecnai T12 electron microscope operating at 120 kV. TEM samples were prepared by dipping a copper grid coated with carbon and formvar (200 mesh, Ted Pella Inc.) into ethanolic particle suspensions and air drying. Scanning electron microscopy (SEM) images were acquired with a JEOL 6700 field emission gun electron microscope operating between 5 and 30 kV depending on magnification and desired image quality. Samples were coated with 10 Å of platinum via sputtering prior to imaging to avoid charging effects. Brightness and contrast were adjusted for clarity on most EM images, but no other image processing was performed. The SEM image in FIG. 1 was cropped slightly on either side without removing key nanoparticle structures.

The SAXSess (Anton-Parr) Kratky camera was used to obtain small-angle X-ray scattering patterns from powdered samples. Scattering from a solid sample holder containing Kapton film (DuPont) windows was collected with a 5 minute exposure time and used as a background pattern. Powdered sample was then densely packed between the windows to yield a sample thickness of approximately 3 mm. Scattering from samples was also collected with 5 minute exposure time, and background scattering was then subtracted from the sample scattering to obtain the raw intensity scattering profiles. All measurements were carried out at room temperature (25° C.). The scattering vector q was calculated from the scattering angle 2θ through $q=4\pi\lambda^{-1} \sin \theta$. Patterns were then de-smeared from the beam profile using measurement of the beam geometry and fitted using the GIFT program (e.g., Bergmann et al., *Journal of Applied Crystallography* 33, 1212 (2000); Glatter, *Journal of Applied Crystallography* 10, 415 (1977); and Glatter, *Journal of Applied Crystallography* 12, 166 (1979)). Pair distance distribution functions (PDDF) were obtained by indirect Fourier transformation of the fitted data.

Synthesis of Exemplary Materials

The synthesis of the exemplary materials disclosed herein is a variation on syntheses of MCM-41 nanoparticles as previously reported (e.g., Lin et al., *Journal of the American Chemical Society* 132, 4834 (2010)). First, 0.145 g of CTAB was added to a 250 mL Erlenmeyer flask and dissolved in 150 g of 0.512 M aqueous $NH_4OH$. Next, decane and DMHA were added in varying amounts (exact amounts and resulting nanoparticle properties can be found in Table 1). The flask was covered tightly with parafilm and sonicated for 1.5 hours. During this time the sonicator heated up, keeping the suspension at roughly 50° C. The flask was removed from the sonicator and allowed to sit undisturbed overnight at room temperature. The suspension was then sonicated once more for 1 hour, transferred to an oil bath at 50° C., and stirred at 700 rpm for 1 hour. Next, 2.5 mL of 0.88 M ethanolic TEOS were added all at once and allowed to react for 1 hour with continuous stirring. Stirring was stopped and the sample was allowed to age for 20 hours at 50° C. To remove excess reagents, the aged suspension was transferred to a Spectrum Labs dialysis tube (MW cutoff of 12,000-14,000) and dialysed against 500 mL 1 M acetic acid in 75:25 water:ethanol for 4 hours, 50:50 water:ethanol for 8 hours, and 25:75 water:ethanol for 16 hours. Finally, the sample was centrifuged at 66,000×g for 15 minutes and redispersed in 99% ethanol three times. Samples were characterized without filtration of final purified product.

Example 2

Silica particles were prepared by a method similar to that described in Example 1, except that gold nanoparticles were added during sonication to provide silica particles that include an outer shell portion having a mesoporous structure forming a cavity, wherein at least a portion of the silica particles include one or more core nanoparticles within the cavity.

Specifically, 3 mL of 2.66 mM CTAB, 3 μL DMHA, and 2.32 μL of decane were stirred rigorously at 50° C. for 30 minutes. After the stirring, the emulsions were subjected to 30 minutes of sonication (20 kHz at 40° C.). While sonicating, various amounts and types of gold nanoparticles (nanorods, spheres, cubes, etc.) that had been previously functionalized with a capture agent of choice (for example, bis-boronic acids for glucose sensing) were added to the sonicating emulsion. Sonication was continued for another 30 minutes. Then, the emulsion/Au solution were equilibrated/stirred at 50° C. for 20 minutes. 30-100 μL of $NH_4OH$ (28-30%) was added, and the mixture was further equilibrated for 5 minutes. Then, 25-50 μL of 0.88 M TEOS was added and the stirring was continued for 60 minutes.

The reaction can be considered finished (ready for purification) here, or additional silane surface chemistry could be included for stability considerations.

Figure 8:
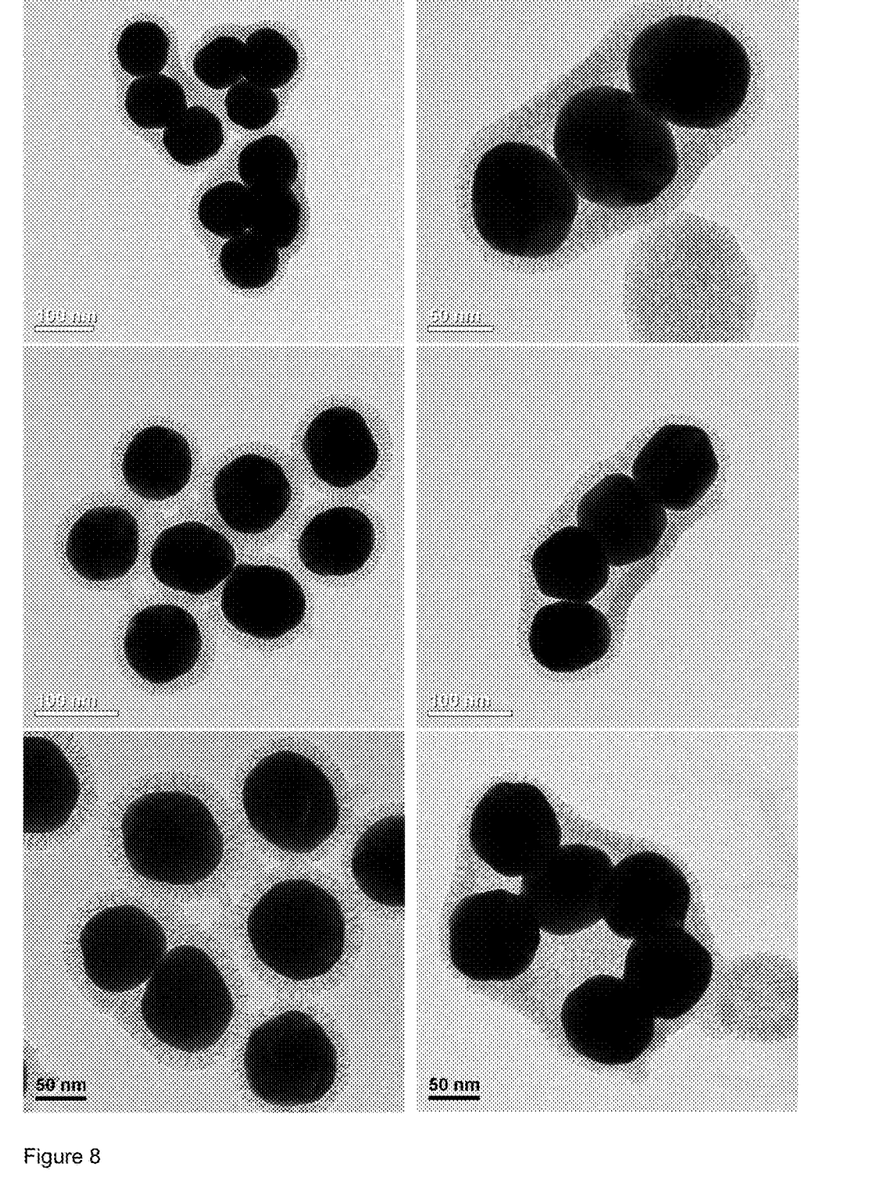
FIG. 8 images from Transmission Electron Microscopy (TEM) of silica particles having from one to six Au nanoparticles within the cavities of the silica particles.

FIG. 8 shows images from Transmission Electron Microscopy (TEM) of the resulting silica particles shows from one to six Au nanoparticles within the cavities of the silica particles.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. Hollow silica particles comprising an outer shell portion having a mesoporous structure, wherein the hollow silica particles have a pore volume of at least 4 $cm^3/g$, wherein the pore volume is determined by nitrogen physisorption at partial pressures of $P/P_o$ of 0.99.

2. The hollow silica particles of claim 1, wherein the hollow silica particles have an average pore diameter of 3 to 100 nm as determined by Barrett-Joyner-Halenda/Kruk-Jaroniec-Sayari (BJH/KJS) nitrogen physisorption measurements, transmission electron microscopy (TEM), and small angle x-ray scattering (SAXS).

3. The hollow silica particles of claim 1, wherein the hollow silica particles have an average particle diameter of 20 to 10,000 nm as determined by transmission electron microscopy (TEM), and a polydispersity index of 0.005 to 0.200 as determined by dynamic light scattering (DLS).

4. The hollow silica particles of claim 1, wherein the hollow silica particles have an outer shell portion with an average thickness of 3 to 100 nm.

5. The hollow silica particles of claim 1, wherein the hollow silica particles have a surface area of at least 1200 m²/g as measured by BET theory.

6. The hollow silica particles of claim 1, wherein the hollow silica particles exhibit a small angle x-ray scattering pattern in which one or more peaks are observed at a diffraction angle corresponding to a range of d=2 to 100 nm.

7. The hollow silica particles of claim 1, wherein a ratio of the thickness of the outer shell portion of the hollow silica particles to the average particle diameter is 0.0003 to 0.8.

8. A method for producing silica particles comprising an outer shell portion having a mesoporous structure, the method comprising:
preparing an aqueous mixture of components comprising at least one quaternary ammonium salt, at least one hydrophobic organic compound, at least one tertiary amine, and an aqueous medium;
agitating the aqueous mixture;
combining at least one silica source capable of forming a silanol compound by hydrolysis thereof with the agitated aqueous mixture under conditions effective to form hollow silica particles according to claim 1;
and removing excess components.

9. The method of claim 8 wherein the method further includes adding nanoparticles before or during agitation, and the method produces silica particles including an outer shell portion having a mesoporous structure forming a cavity, and wherein at least a portion of the silica particles include one or more core nanoparticles within the cavity.

10. The method of claim 8, wherein the at least one quaternary ammonium salt is selected from the group consisting of a compound represented by the formula (1) and a compound represented by the formula (2):

$$[R^1(CH_3)_3N]^+X^- \quad (1)$$

$$[R^1R^2(CH_3)_2N]^+X^- \quad (2),$$

wherein $R^1$ and $R^2$ are each independently a linear or branched alkyl group having 4 to 22 carbon atoms; and X is a monovalent anion.

11. The method of claim 8, wherein the at least one tertiary amine is selected from the group consisting of a compound represented by the formula (3) and a compound represented by the formula (4):

$$R^1(CH_3)_2N \quad (3)$$

$$R^1R^2(CH_3)N \quad (4),$$

wherein $R^1$ and $R^2$ are each independently a linear or branched alkyl group having 4 to 22 carbon atoms.

12. The method of claim 8, wherein the at least one hydrophobic organic compound is selected from the group consisting of hydrocarbon compounds, ester compounds, fatty acids having 6 to 22 carbon atoms, and alcohols having 6 to 22 carbon atoms.

13. The method of claim 12, wherein the at least one hydrophobic organic compound is a hydrocarbon compound selected from the group consisting of decane, squarane, squalene, perhydrosqualene, trimethyl benzene, triisopropyl benzene, isomers of xylene, toluene, benzene, a liquid paraffin, or a liquid petroleum jelly, and combinations thereof.

14. The method of claim 8, wherein the aqueous medium comprises aqueous ammonium hydroxide.

15. The method of claim 8, wherein the at least one silica source is selected from the group consisting of compounds represented by the following formulas (4), (5), (6), and (7):

$$R^3SiY_3 \quad (4);$$

$$R^3_2SiY_2 \quad (5);$$

$$R^3_3SiY \quad (6); \text{ and}$$

$$Y_3Si-R^4-SiY_3 \quad (7),$$

wherein $R^3$ groups are each independently an organic group having a carbon atom directly bonded to a silicon atom; $R^4$ is a hydrocarbon group having 1 to 4 carbon atoms or a phenylene group; and Y is a monovalent hydrolyzable group that can be hydrolyzed into a hydroxyl group.

16. A method of using hollow silica particles comprising one or more of:
providing hollow silica particles according to claim 1 to support a catalyst;
providing hollow silica particles according to claim 1 as an adsorbent;
providing hollow silica particles according to claim 1 to separate a plurality of materials;
providing hollow silica particles according to claim 1 to deliver at least one drug; and
providing hollow silica particles according to claim 1 to adsorb environmental contaminants.

17. A method for high contrast biological/biomedical imaging comprising:
providing hollow silica particles according to claim 1; and
chemically modifying the hollow silica particles to enhance the contrast.

18. The method of claim 8, wherein agitating comprises sonicating.

19. The method of claim 18, wherein sonicating comprises sonicating at a temperature of 5 to 95° C.

20. The method of claim 8, wherein agitating comprises stirring.

21. The method of claim 8, wherein agitating comprising stirring and sonicating.

* * * * *